(12) United States Patent
Lee et al.

(10) Patent No.: US 9,123,097 B2
(45) Date of Patent: Sep. 1, 2015

(54) SYSTEM AND METHOD FOR AUTOMATIC GENERATION OF INITIAL RADIATION TREATMENT PLANS

(75) Inventors: Michael Chun-Chieh Lee, Bronx, NY (US); Lilla Boroczky, Mount Kisco, NY (US)

(73) Assignee: Koninklijke Philips N.V., Eindhoven (NL)

( * ) Notice: Subject to any disclaimer, the term of this patent is extended or adjusted under 35 U.S.C. 154(b) by 247 days.

(21) Appl. No.: 13/995,630

(22) PCT Filed: Dec. 7, 2011

(86) PCT No.: PCT/IB2011/055507
§ 371 (c)(1),
(2), (4) Date: Jun. 19, 2013

(87) PCT Pub. No.: WO2012/085722
PCT Pub. Date: Jun. 28, 2012

(65) Prior Publication Data
US 2013/0272593 A1    Oct. 17, 2013

Related U.S. Application Data

(60) Provisional application No. 61/424,845, filed on Dec. 20, 2010.

(51) Int. Cl.
*A61N 5/10* (2006.01)
*G06F 19/00* (2011.01)
*G06T 7/00* (2006.01)

(52) U.S. Cl.
CPC .............. *G06T 7/0012* (2013.01); *A61N 5/103* (2013.01); *G06F 19/34* (2013.01); *G06F 19/3443* (2013.01); *A61N 2005/1041* (2013.01); *G06T 2207/30016* (2013.01)

(58) Field of Classification Search
CPC ..... G06F 19/34; G06F 19/3443; A61N 5/103; A61N 5/00; A61B 6/00; G06K 9/6215; G06K 9/64
See application file for complete search history.

(56) References Cited

U.S. PATENT DOCUMENTS 7,773,788 B2 * 8/2010 Lu et al. .................... 382/128
8,232,535 B2 * 7/2012 Olivera et al. ............ 250/493.1
(Continued)

FOREIGN PATENT DOCUMENTS

| EP | 1362616 A1 | 11/2003 |
|----|------------|---------|
| WO | 2009083841 A1 | 7/2009 |
| WO | 2010018477 A2 | 2/2010 |

OTHER PUBLICATIONS

Kazhdan M. et al. "A Shape Relationship Descriptor for Radiation Therapy Planning". Sep. 20, 2009. Medical Image Computing and Computer-Assisted Intervention A Miccai. Springer Berlin Heidelberg, pp. 100-108. ISBN: 978-3-642-04270-6.
Berger, J. Ed. Roentgen: Case-based Reasoning and Radiation therapy Planning. Institute of Electrical and Electronics Engineers. Proceedings of the Conference on Artificial Intelligence for Applications, Mar. 1, 1994, pp. 210-214.

(Continued)

*Primary Examiner* — Utpal Shah

(57) ABSTRACT

A non-transitory computer-readable storage medium storing a set of instructions executable by a processor. The set of instructions is operable to receive a current patient medical image of a current patient, compare the current patient medical image to a plurality of previous patient medical images, each of the previous patient medical images corresponding to a previous patient, select one of the previous patients based on a geometric similarity between the previous patient medical image of the selected one of the previous patients and the current patient medical image, and determine an initial radiation treatment plan based on a radiation treatment plan of the selected one of the previous patients.

15 Claims, 3 Drawing Sheets

(56) References Cited

U.S. PATENT DOCUMENTS

| | | |
|---|---|---|
| 2006/0100738 A1 | 5/2006 | Alsafadi et al. |
| 2007/0156453 A1 | 7/2007 | Frielinghaus et al. |
| 2008/0310590 A1* | 12/2008 | Meyer et al. ............ 378/65 |
| 2010/0177871 A1* | 7/2010 | Nord .................. 378/65 |
| 2011/0202361 A1* | 8/2011 | Firminger et al. ........ 705/2 |
| 2012/0041779 A1* | 2/2012 | Boroczky et al. ........ 705/2 |
| 2014/0378737 A1* | 12/2014 | Carpenter et al. ........ 600/1 |

OTHER PUBLICATIONS

Willy, PM et al. "Content-based medical image retrieval (CBMIR): an intelligent retrieval system for handling multiple organs of interest". Computer-Based Medical Systems, 2004, CMBS Proccedings 17th IEEE Symposium.

* cited by examiner

SYSTEM AND METHOD FOR AUTOMATIC GENERATION OF INITIAL RADIATION TREATMENT PLANS

BACKGROUND

Radiation therapy plans are generated based in large part on a patient's physical parameters. The design of the plan may be complicated as numerous treatment parameters can be defined to address the particular physical characteristics of the patient. If an initial candidate radiation treatment plan can be efficiently devised, overall quality of care may increase correspondingly as it may be simpler and faster for caregivers or computers to modify this initial candidate plan into the final course of treatment that will be used to treat the patient.

SUMMARY OF THE INVENTION

A non-transitory computer-readable storage medium stores a set of instructions executable by a processor. The set of instructions is operable to receive a current patient medical image of a current patient. The set of instructions is further operable to compare the current patient medical image to a plurality of previous patient medical images. Each of the previous patient medical images corresponds to a previous patient. The set of instructions is further operable to select one of the previous patients based on a geometric similarity between the previous patient medical image of the selected one of the previous patients and the current patient medical image. The set of instructions is further operable to determine an initial radiation treatment plan based on a radiation treatment plan of the selected one of the previous patients.

A system includes a medical imager, a previous patient database, a similarity search system, and a plan generation system. The medical imager generates a current patient medical image for a current patient. The previous patient database stores data relating to a plurality of previous patients. The data relating to each of the previous patients includes a medical image relating to each of the previous patients and a radiation treatment plan relating to each of the previous patients. The similarity search system determines a similarity score for each of the plurality of previous patients. The similarity score for each of the previous patients is determined based on a geometric similarity between the medical image corresponding to each of the previous patients and the current patient medical image. The plan generation system determines an initial radiation treatment plan for the current patient based on a radiation treatment plan for a selected one of the plurality of previous patients. The selected one of the plurality of previous patients is selected based on the similarity score of the selected one of the plurality of previous patients.

DETAILED DESCRIPTION

Figure 1:
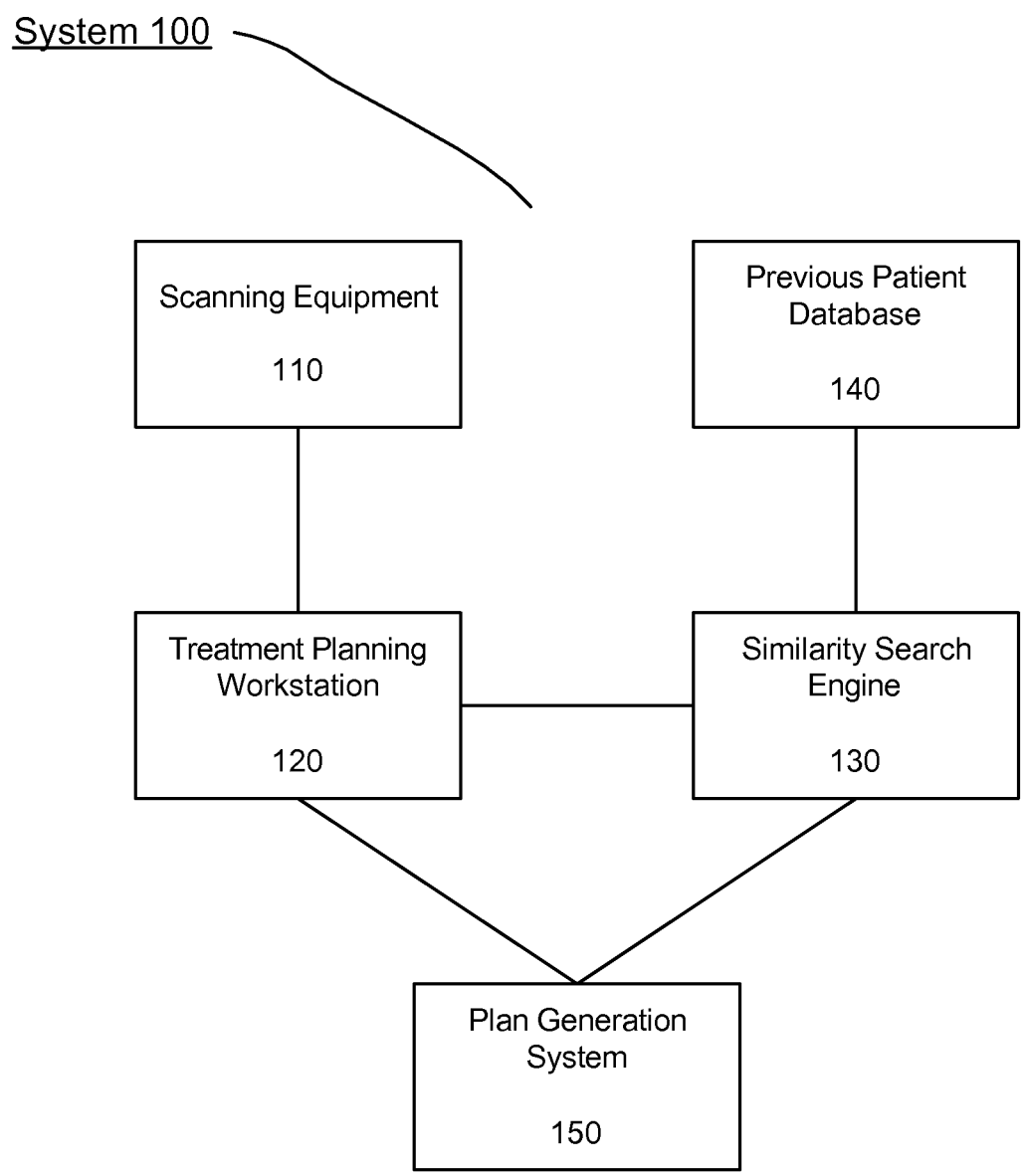
FIG. 1 illustrates a system for automatic generation of initial radiation treatment plans according to an exemplary embodiment.

The exemplary embodiments of the present invention may be further understood with reference to the following description and the appended drawings, wherein like elements are referred to with the same reference numerals. The exemplary embodiments describe systems and methods by which initial radiation treatment plans for a patient receiving radiation therapy are automatically generated.

Prior to initiating radiation therapy for a patient, a number of steps must be taken. A radiation oncologist, dosimetrist, or other appropriate medical professional (referred to herein as a "planner") must identify the target volume to be irradiated, as well as organs and tissues to be spared from radiation (also referred to herein as "organs at risk"). These areas are typically indicated on computed tomography (CT) images, magnetic resonance images (MRI), positron emission tomography (PET) images, x-ray images, single photon emission computed tomography (SPECT) images, or ultrasound images, and may be drawn with or without computer assistance in defining their boundaries. The planner may further define constraints on the amount of radiation to be delivered to target and healthy tissue. Once this has been determined, the modality (e.g., photon, electron), quantity, beam orientation, beam energy and beam modifiers (e.g., blocks, wedges) of the radiation sources are then set to define an initial candidate treatment plan.

The planning process then proceeds iteratively from this candidate treatment plan. At the initial step and each subsequent step, the radiation dose resulting from the plan is computed throughout the patient volume. The parameters of the radiation therapy, as discussed above, are then adjusted iteratively until the desired dose constraints are achieved and the planner judges the plan to be satisfactory. The above framework applies both to 3D conformal radiation therapy (3DCRT) and intensity modulated radiation therapy (IMRT). The adjustment process may proceed with or without computer assistance in determining the updates to the parameters of the radiation therapy plan. The definition of the initial plan by the planner is important because a well-designed initial plan may reduce the time required to optimize treatment for the patient. Further, the quality of the final radiation therapy plan may vary depending on the quality of the manually-created initial plan, leading to the potential for variation in quality of care depending on the caregiver. The exemplary embodiments address these flaws by using patient geometry and other parameters to automatically generate an initial therapy plan.

FIG. 1 illustrates a schematic view of an exemplary system 100. The lines connecting the elements shown in FIG. 1 may be any type of communications pathway suitable for conveying data between the elements so connected. The system 100 includes scanning equipment 110 for obtaining images of a current patient for whom radiation treatment is currently being planned. The scanning equipment 110 may be a CT scanner, an MRI imager, a PET imager, an x-ray scanner, a SPECT imager, an ultrasound imager, or may be any of the various other types of medical imaging devices known in the art. The scanning equipment 110 is communicatively coupled with a treatment planning workstation 120, which is a computing system (e.g., a combination of hardware and software such as a processor and software instructions which are executable by the processor to carry out certain functions) used by a planner to plan radiation treatment for the current patient. The treatment planning workstation 120 is similar to known systems presently used by planners, except as will be described hereinafter.

The treatment planning workstation 120 receives patient images from the scanning equipment 110 and transmits the patient images to a similarity search engine 130. The similarity search engine 130 also retrieves data on previous patients from a previous patient database 140, which is then compared to the images of the current patient as will be described in further detail hereinafter. It is possible the previous patient database 140 to store information in a repository using known medical informatics standards such as DICOM or DICOM-RT. Data stored for previous patients may include medical images (e.g., CT, MRI, PET, x-ray, SPECT, ultrasound, etc.), geometric definition of the target structure (e.g., a tumor to be irradiated), identification of organs at risk (e.g., organs that should not be irradiated), and a treatment plan used for the prior patient. This includes the modality of radiation, the number of radiation sources, the energy of each beam, modifiers used, and intensity maps. In some instances, the radiation treatment plan stored for each previous patient is a final treatment plan that has concluded after the initial treatment plan for the patient has been refined. Additionally, the information stored in the previous patient database 140 for each patient may include further relevant information such as age, patient medical history, patient's family medical history, further information about the patient's current condition, other treatment currently being administered to the patient (e.g., chemotherapy), or any other information that may be relevant for the planner to design a course of radiation treatment for the current patient.

Some or all of the data relating to previous patients is then transmitted from the similarity search engine 130 to a plan generation system 150, which generates a plan for the current patient based on the data relating to previous patients, as will be described in farther detail hereinafter. The plan generation system 150 is also coupled with the treatment planning workstation 120, in order that its output may be returned to the planner who is using the treatment planning workstation. Those of skill in the art will understand that the similarity search engine 130, the previous patient database 140, and the plan generation system 150 may be implemented in various ways, including as elements of the treatment planning workstation 120, or as separate hardware and/or software components, without impacting their functions, or any combinations thereof. For example, the similarity search engine 130 may include a processor and software containing instructions executable by the processor. The previous patient database 140 may be embodied on a server having a storage device array and a relational database, or other type of commonly used database structure.

Figure 2:
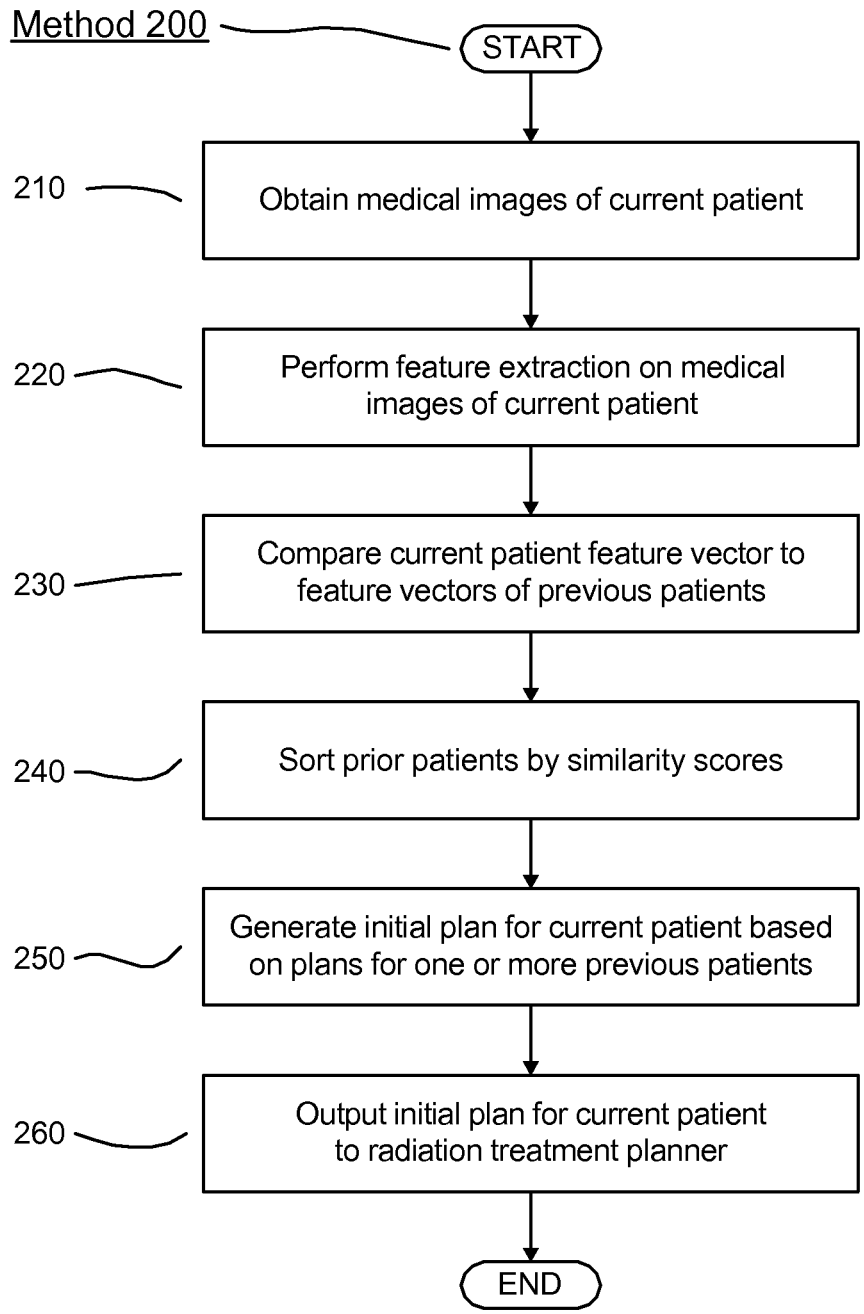
FIG. 2 illustrates a method for automatic generation of initial radiation treatment plans according to an exemplary embodiment.

FIG. 2 illustrates an exemplary method 200 for automatically generating an initial radiation treatment plan for a current patient, which will be described herein with reference to the exemplary system 100 of FIG. 1. In step 210, the scanning equipment 110 is used to obtain images of the current patient. As discussed above, the images obtained may be CT images, MRI images, or any other type of medical imaging. Typically, the images are a series of two-dimensional cross-sections from which a three-dimensional representation of the patient may be understood. However, in some cases it may be appropriate to include the use of a single two-dimensional image, or to include the use of a three-dimensional model, without departing from the broader concepts described by the exemplary embodiment. Alternatively, the current patient medical images may have been previously recorded, using a device such as the scanning equipment 110, and may be retrieved at this stage of the method 200.

In step 220, feature extraction is performed on the current patient images using the similarity search engine 130. This may involve the identification of various structures (e.g., tumors, organs, bones, etc.) indicated by the images, and determination of the volumes, shape, morphology and texture of each of the features. This proceeds using feature extraction algorithms, many of which are known in the art, and results in the generation of a feature vector representing a plurality of features indicated in the current patient images.

In step 230, the current patient's feature vector is compared to feature vectors of previous patients, for whom relevant data is stored in the previous patient database 140. In the exemplary embodiment, feature extraction results for previous patients are stored in the form of feature vectors in the previous patient database 140; in another embodiment, data stored in the previous patient database 140 are images relating to previous patients, and feature vectors may be computed at this stage of the exemplary method. In this step, the similarity search engine 130 compares the current patient's feature vector to a feature vector relating to each of a plurality of prior patients; comparison proceeds using known metrics, which may include an Lp-norm of the vector difference (e.g., city block distance, Mahalanobis distance, Euclidean distance, and higher order extensions). The result of this comparison is a numerical value describing the similarity of each of the previous patients being evaluated to the current patient. For example, this may be a number on a scale of 0 to 100, 0 to 1, etc.

Alternatively, rather than performing feature extraction, the images of the current patient and the prior patient are directly geometrically compared. As one example, this involves the use of a translation and rotation invariant Hausdorff distance metric. In another example, this involves the alignment of images to a common atlas by non-rigid registration, and comparison on a voxel-by-voxel basis. The comparison may be applied to each structure in the image (e.g., target volume, organ at risk, etc.), to one or more points contained within the structure (e.g., the centroid of each structure), to the boundaries of each structure, or to the combination of all structures at once. Those of skill in the art will understand that an embodiment that does not involve the comparison of feature vectors may lack the feature extraction step 220 described above. As above, the result of this comparison is a similarity score, and may be, for example, a number on a scale of 0 to 100, 0 to 1, etc.

As a further example, the comparison step 230 can involve both the comparison of patients as represented by feature vectors, and the comparison of the images as a whole. In this example, the two similarity scores are combined (e.g., by using the mean of the two similarity scores relating to each prior patient, or using another method).

As a further option, additional features not computed from the images can be included in the feature comparison process, described above. These features may include biomarker data, data relating to family history (e.g., the presence of genes that may indicate increased susceptibility to radiation), age of the patient, history of prior cancer in the patient or the patient's family, presence of other ongoing therapies (e.g., chemotherapy), etc. In such case, these are simply included in the application of the feature comparison engine, without significantly changing the nature of the process described above.

After comparison of the current patient to prior patients, as described above, in step 240 the prior patients are sorted by their corresponding similarity scores. Next, in step 250, an initial plan is generated for the current patient by the plan generation system 150. In a first example, the plan generation system 150 copies the plan from the previous patient with the highest similarity score for use with the current patient. As described above, a plan may include the modality of radiation (e.g., photon, electron, proton), the number of beams/sources, the angular orientation of the beams, the isocenter position within the patient for each beam, the energy of each beam, the use of modifiers (e.g., wedges, dynamic wedges, filters), and the intensity maps. This then becomes the initial plan for the current patient, and may be refined as described above.

In another alternative example, the plan generation system 150 combines the plans from multiple previous patients. In such an example, one or more of the plan elements (e.g., modality, number of beams, etc.) for the plan for the current patient are generated by combining values from one or more of the previous patients. For example, an angular orientation of one or more of the beams is taken from a weighted average of a group of prior similar patients, with each prior patient weighted by their similarity score to the current patient. In another example, the combination is based on majority votes or on median values. The number of prior patients to be composited and the selection of features to be composited may vary among different implementations; in one example, the planner selects these options.

In another alternative example, the selection of past patients is filtered based on outcomes; for example, only patients with good clinical outcomes are used. In such an example, the previous patient database 140 additionally stores data relating to outcomes. Outcomes may be quantified as years of survival, years of disease-free survival, time to progression, etc. In another example, the plan generation system 150 also copies dose constraints from prior patients, either by using a dose constraint from a most similar prior patient or using a composite of a plurality of prior patients as described above.

Finally, in step 260, the plan that has been generated by the plan generation system 150 is transmitted to the treatment planning workstation 110. At this point, refinement of this automatically generated initial treatment plan proceeds as usual.

Figure 3:
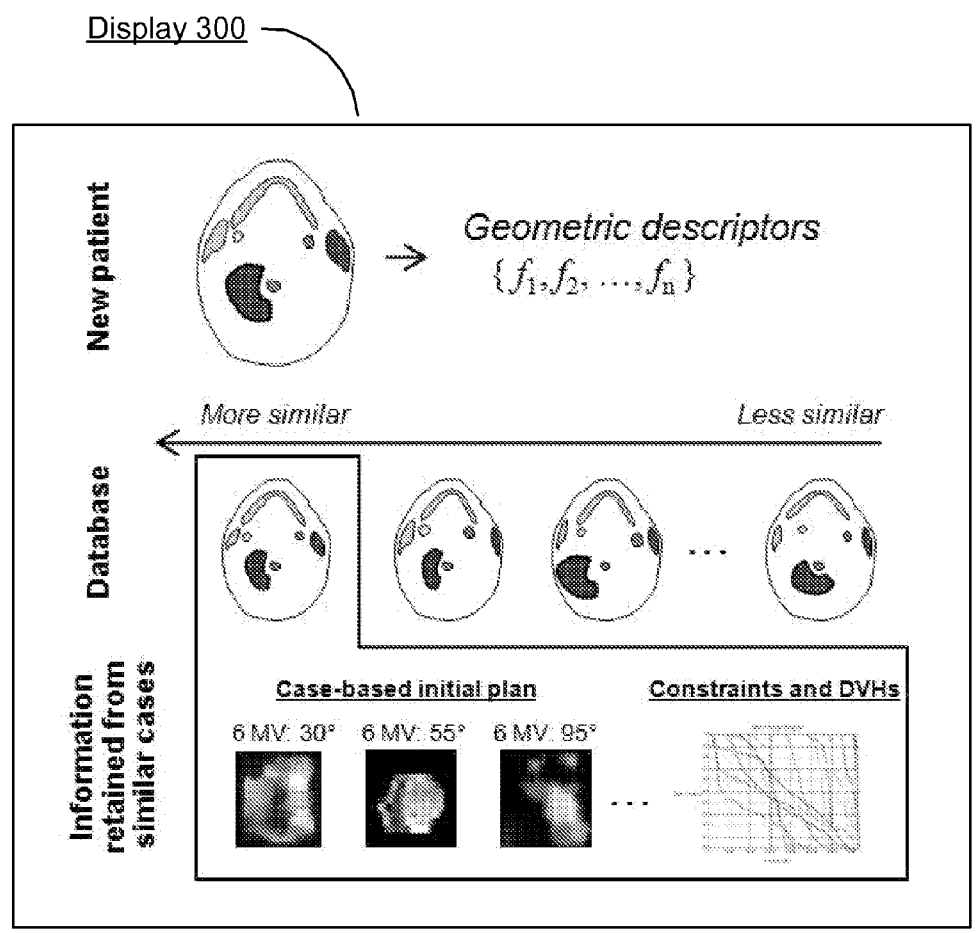
FIG. 3 illustrates a display of radiation treatment plans for current and prior patients according to an exemplary embodiment.

FIG. 3 illustrates an exemplary display 300 that is provided to a planner using the treatment planning workstation 110. The display 300 includes an illustration of the geometric features of the current patient. The display 300 also includes an illustration of geometric features of previous patients ranked by similarity. The planner may select one of the previous patients for further viewing, and the display 300 further shows the stored radiation treatment plan for the selected one of the previous patients. For example, in the illustrated display 300, the most similar previous patient is selected for display.

The exemplary embodiments result in the generation of an initial radiation treatment plan for the current patient that is of a greater quality than one that is created by the planner on an ad hoc basis based on the planner's own experience. Further, because of the objective nature of the comparison to past patients, the quality of care received by patients may be standardized, rather then dependent upon the skills and experience of the planner. Additionally, because the initial plan for the current patient is based on one or more previous patients sharing characteristics with the current patient, less refinement may be required, resulting in the patient being subjected to less radiation overall and completing the course of radiation treatment sooner.

Those skilled in the art will understand that the above-described exemplary embodiments may be implemented in any number of manners, including, as a separate software module, as a combination of hardware and software, etc. For example, the similarity search engine 130 may be a program containing lines of code that, when compiled, may be executed on a processor.

It is noted that the claims may include reference signs/numerals in accordance with PCT Rule 6.2(b). However, the present claims should not be considered to be limited to the exemplary embodiments corresponding to the reference signs/numerals.

It will be apparent to those skilled in the art that various modifications may be made in the present invention, without departing from the spirit or the scope of the invention. Thus, it is intended that the present invention cover modifications and variations of this invention provided they come within the scope of the appended claims and their equivalents.

The invention claimed is:

1. A non-transitory computer-readable storage medium storing a set of instructions executable by a processor, the set of instructions being operable to:

receive a current patient medical image of a current patient;

compare the current patient medical image to a plurality of previous patient medical images, each of the previous patient medical images corresponding to a previous patient;

select one of the previous patients based on a geometric similarity between the previous patient medical image of the selected one of the previous patients and the current patient medical image; and determine an initial radiation treatment plan based on a radiation treatment plan of the selected one of the previous patients wherein a plurality of the previous patients are selected based on a geometric similarity between the previous patient medical images of the selected previous patients and the current patient medical image, and wherein the initial radiation treatment plan is determined based on a radiation treatment plan of each of the selected plurality of previous patients, wherein an element of the initial radiation treatment plan is based on a weighted average of corresponding elements of the radiation treatment plans of each of the selected plurality of previous patients, wherein the weighted average is weighted based on a similarity score of each of the selected plurality of previous patients, and wherein the similarity scores are based on a geometric similarity of the current patient medical image to each of the previous patient medical images.

2. The non-transitory computer-readable storage medium of claim 1, wherein the geometric similarity is determined by one of a translation and rotation invariant Hausdorff distance metric and a voxel-by-voxel comparison, and wherein the current patient medical images are one of CT images, MRI images, PET images, x-ray images, SPECT images and ultrasound images.

3. The non-transitory computer-readable storage medium of claim 1, wherein the geometric similarity is determined by comparing one of A) each of a plurality of the structures of the current patient medical image to each of a plurality of structures of the previous patient medical image, B) a centroid of each of the structures of the current patient medical image to a centroid of each of the structures of the previous patient medical image, C) a boundary of each of the structures of the current patient medical image to a boundary of each of the structures of the current patient medical images, and D) a combination of all of a plurality of structures of the current patient medical image to a combination of all of a plurality of structures of the previous patient medical image.

4. The non-transitory computer-readable storage medium of claim 1, wherein selecting one of the previous patients comprises:

determining a current patient feature vector for the current patient medical image;

determining a previous patient feature vector for each of the previous patient medical images; and comparing the current patient feature vector to each of the previous patient feature vectors, wherein the current patient feature vector and the previous patient feature vector comprise a plurality of features selected from the group comprising: features selected from a medical image, features describing the geometric characteristics of the image, features relating to biomarker data, features relating to family history, features relating to the presence of genes that may indicate increased susceptibility to radiation, features relating to an age of the patient, features relating to a race of the patient, features relating to a history of prior cancer in the patient, features relating to a history of prior cancer in the patient's family, features relating to a concurrent therapy, and features relating to a medical history of the patient with respect to cancer or co-morbidities.

5. The non-transitory computer-readable storage medium of claim 1, wherein the comparing the current patient feature vector to each of the previous patient feature vectors is based on an Lp-norm of a vector difference between the current patient feature vector and each of the previous patient feature vectors, and wherein the vector difference is one of a city-block distance, a Mahalanobis distance, and a Euclidean distance.

6. The non-transitory computer-readable storage medium of claim 1, wherein a similarity score is generated for each of the previous patient medical images based on the geometric similarity of the current patient medical image to each of the previous patient medical images, and wherein the selected one of the previous patients is the one of the previous patients corresponding to a highest one of the similarity scores.

7. The non-transitory computer-readable storage medium of claim 1, wherein an element of the initial radiation treatment plan that is based on radiation treatment plan of the selected one of the previous patients is one of a radiation modality, a number of sources, a beam intensity, a beam modifier, an intensity map, and a dose constraint.

8. The non-transitory computer-readable storage medium of claim 1, wherein determining the initial radiation treatment plan comprises copying the radiation treatment plan of the selected one of the previous patients.

9. A system, comprising:
a medical imager generating a current patient medical image for a current patient;
a previous patient database storing data relating to a plurality of previous patients, the data relating to each of the previous patients including a medical image relating to each of the previous patients and a radiation treatment plan relating to each of the previous patients;
a similarity search system determining a similarity score for each of the plurality of previous patients, the similarity score for each of the previous patients being determined based on a geometric similarity between the medical image corresponding to each of the previous patients and the current patient medical image; and
a plan generation system determining an initial radiation treatment plan for the current patient based on the radiation treatment plan relating to a selected one of the plurality of previous patients, the selected one of the plurality of previous patients being selected based on the similarity score of the selected one of the plurality of previous patients, wherein a plurality of the previous patients are selected based on a geometric similarity between the previous patient medical images of the selected previous patients and the current patient medical image, and wherein the initial radiation treatment plan is determined based on a radiation treatment plan of each of the selected plurality of previous patients, wherein an element of the initial radiation treatment plan is based on a weighted average of corresponding elements of the radiation treatment plans of each of the selected plurality of previous patients, wherein the weighted average is weighted based on a similarity score of each of the selected plurality of previous patients, and wherein the similarity scores are based on a geometric similarity of the current patient medical image to each of the previous patient medical images.

10. The system of claim 9, wherein the medical imager is one of a CT imager and an MRI imager, a PET scanner, an x-ray imager, a SPECT scanner and ultrasound system.

11. The system of claim 9, wherein the previous patient database uses one of a DICOM standard and a DICOM-RT standard.

12. The system of claim 9, further comprising:
a treatment planning workstation receiving the initial radiation treatment plan from the plan generation system and providing the initial radiation treatment plan to a user.

13. The system of claim 9, wherein determining a similarity score comprises:
determining a current patient feature vector for the current patient medical image;
determining a previous patient feature vector for each of the previous patient medical images; and
comparing the current patient feature vector to each of the previous patient feature vectors.

14. The system of claim 13, wherein the current patient feature vector and the previous patient feature vector comprise a plurality of features selected from the group comprising: features selected from a medical image, features describing the geometric characteristics of the image, features relating to biomarker data, features relating to family history, features relating to the presence of genes that may indicate increased susceptibility to radiation, features relating to an age of the patient, features relating to a race of the patient, features relating to a history of prior cancer in the patient, features relating to a history of prior cancer in the patient's family, features relating to a concurrent therapy, and features relating to a medical history of the patient with respect to cancer or co-morbidities.

15. The system of claim 13, wherein the comparing the current patient feature vector to each of the previous patient feature vectors is based on an Lp-norm of a vector difference between the current patient feature vector and each of the previous patient feature vectors, wherein the vector difference is one of a city-block distance, a Mahalanobis distance, and a Euclidean distance.

* * * * *